(12) United States Patent
Keskinen et al.

(10) Patent No.: US 6,401,553 B1
(45) Date of Patent: Jun. 11, 2002

(54) METHOD FOR MINIMIZING COULOMBIC LOSSES IN ELECTRICAL IMPACTORS AND AN ELECTRICAL IMPACTOR

(75) Inventors: Jorma Keskinen; Annele Virtanen, both of Tampere (FI)

(73) Assignee: Dekati Oy, Tampere (FI)

( * ) Notice: Subject to any disclaimer, the term of this patent is extended or adjusted under 35 U.S.C. 154(b) by 0 days.

(21) Appl. No.: 09/380,494
(22) PCT Filed: Jan. 26, 1999
(86) PCT No.: PCT/FI99/00050
§ 371 (c)(1),
(2), (4) Date: Sep. 14, 1999
(87) PCT Pub. No.: WO99/37990
PCT Pub. Date: Jul. 29, 1999

(30) Foreign Application Priority Data

Jan. 27, 1998 (FI) .................................................. 980178

(51) Int. Cl.[7] .............................................. G01N 15/02
(52) U.S. Cl. ...................... 73/865.5; 324/71.4; 324/464
(58) Field of Search ....................... 73/865.5; 324/71.4, 324/464

(56) References Cited

U.S. PATENT DOCUMENTS 4,312,180 A * 1/1982 Reif et al. .................. 73/865.5
4,837,440 A    6/1989 Burtscher et al. ....... 324/464 X
RE36,074 E  * 2/1999 Kouzuki et al. ............ 73/865.5

FOREIGN PATENT DOCUMENTS

DE        3104878 A1    8/1982 .......... G01N/15/02

OTHER PUBLICATIONS

Electrostatic Effects in Inertial Impactors; De Juan L et al.; J Aerosol Sci; Journal of Aerosol Science; Sep. 1997; vol. 28, No. 6. Abstract Only—XP–002101477.

Low Pressure Impactor with Electrical Concentration Detection; Keskinen J. et al.; J Aerosol Sci; Journal of Aerosol Science; vol. 22, No. suppl1; Sep. 16–20, 1991; Abstract Only—XP–002101478.

* cited by examiner

*Primary Examiner*—Thomas P. Noland
(74) *Attorney, Agent, or Firm*—Burns, Doane, Swecker & Mathis, L.L.P.

(57) ABSTRACT

The subject of the invention is a method for minimizing Coulombic losses in impactors and an impactor, in which Coulombic losses have been minimized. The method according to the invention is based on restricting the force effect of the charges accumulated in impactor's insulators on the charged particles. This restriction of the force effect can be realized, for example, by placing an electrically conductive surface between the insulator and the flow, or by forming an insulator so that the force effect is minimized.

10 Claims, 5 Drawing Sheets

METHOD FOR MINIMIZING COULOMBIC LOSSES IN ELECTRICAL IMPACTORS AND AN ELECTRICAL IMPACTOR

BACKGROUND OF THE INVENTION

1. Field of the Invention

The subject of the invention is a method and an apparatus for measuring particle size distribution with an electrical impactor.

The subject of the invention is also an electrical impactor.

2. Background Information

As environmental standards are becoming stricter, the need for real-time measurement of particulate emissions increases. This need for measurement is especially important in the development of purification methods, in the research on different combustion processes as well as in the monitoring processes of the actual emissions. Traditionally, the so-called cascade impactors have been used in particle measurement. These impactors classify particles according to particle size.

Traditional cascade impactors do not allow for real-time measurement of particle size distribution and their changes. An electrical impactor, which has been developed from the traditional cascade impactor, has enabled this real-time measurement of particle size distribution.

FIG. 1 represents the operating principle of a known electrical impactor. The pump 14 produces underpressure, which then sucks the airflow 11 under observation first to the charger 12, in which the particles are charged. Then, the airflow containing these charged particles is sucked through an impactor 10, which consists of several stages. Charged particles, which are left behind on each of the stages, produce an electric current, which is then measured separately on each of the levels with a sensitive current meters located in current measurement unit 15. The functions of the charger 12, current measurement unit 15 and the pump 14 are controlled from the control unit 16.

FIG. 2 presents a cross section of an electrical low pressure impactor, in which the chambers 29a and 29b can be seen, which are connected to the impactor's first two stages 20a and 20b. Airflow 21 is brought through the impactor's frame part 25 to the first chamber 29a through the inlet hole 28. Each of the stages have a nozzle part 22a; 22b. The airflow 21 carrying the particles flows through the outlets of the nozzle parts. Behind the nozzle parts 22a; 22b lie the collector surfaces 23a; 23b. The collector surface has at least one outlet 30, through which the flow 21 can flow to the next chamber or out of the impactor. Insulators 24a; 24b; 24c, which are situated between stages 20a; 20b, insulate different stages 20a, 20b from each other and from the cover section 26 of the impactor's first stage.

FIG. 3 presents a detail of the collector surface 23. The direction of the airflow 21 flowing through the outlets of the nozzle part changes radically as it reaches the collector surface 23. Particles 31 with a sufficiently low mechanical mobility are transported by the airflow 21 and cannot follow the radical and sudden change of the direction and impinge the collector surface 23. The particles 31, which have impinged the collector surface 23, collect on the collector surface 23 and form a mass 32.

As the charged particles impinge the collector surface 23a; 23b, as described in FIG. 2, they produce a change in the collector surface's charge level. Because the collector surface 23a; 23b is electrically connected to the impactor's stage in question 20a; 20b, which is, furthermore, connected to the current measurement unit 15 with an electric connection 27a; 27b, the change in the charge level of the collector surface 23a; 23b manifests itself as electric current, which can be perceived with the help of sensitive current meters, which are situated in the current measurement unit 15.

The particles' mechanical mobility depends on their size in a known manner. This enables size selective classification of the particles. By choosing in a known manner the number and the size of holes in the nozzle parts 22a and 22b, the distance between the nozzle part 22a; 22b and the collector surface 23a; 23b and the velocity of the flow can each of the impactor's stages 20a, 20b be designed so, that on each stage the collector surface 23a; 23b draws only those particles with a mechanical mobility value lower than the desired value, or in other words, particles which are larger than a certain, set particle size.

FIG. 4a presents the collection efficiency 42 of a stage of impactor as function of the particle size (Dp). FIG. 4a describes the collection efficiency of such an impactor stage, whose cut-off point is set at 1 $\mu$m. In an ideal situation, the collection efficiency of this stage would be step-like, but, due to non-ideal situations, in practise some particles which are larger than the cut-off point will pass the stage in question, and some particles which are smaller than the cut-off point will collect to the stage. This manifests itself as a deviation from the step-like shape of the efficiency curve 42.

Certain collection efficiency, as demonstrated for example in FIG. 4b, can be achieved by sequentially placing stages with a different cut-off point. An impactor with collection efficiency as demonstrated in FIG. 4b has a first stage (collection efficiency curve 44), which collects particles over 100 $\mu$m, a second stage (curve 43), which collects particles between 10–100 $\mu$m and, correspondingly, a third and a fourth stage (curves 42 and 41), which collect particles between 1–10 $\mu$m and 0.1–1 $\mu$m.

When the cut-off points of impactor's (10) different stages 20a, 20b and the average charge received by the particles at the charger 12 as a function of the particle size are known, size distribution of particles contained in the flow 11 can be determined real-time according to currents received by the current measurement unit 15 from each of the stages 20a, 20b.

The problem of an electrical impactor construed according to the prior art as described above is the loss of smaller particles in the stages of impactor, which collect larger particles. Due to these losses impactor's collection efficiencies 41, 42, 43, 44 can be significant to those particles which are much smaller than the cut-off point. Collection efficiency curves 41, 42, 43, 44 presented in FIGS. 4a and 4b demonstrate this problem: the curves do not zero in the sizes smaller than the cut-off point.

The inventors have noticed that a significant part of small particle losses in stages collecting larger particles are due to the accumulation of charges in the insulator between stages of impactor and to the Coulombic losses caused by these charges. These new discoveries by the inventors are represented in FIGS. 5 and 6, which illustrate how the effects on forces, which are caused by Coulombic interaction, produce the above-mentioned losses of small particles. FIG. 5 presents impactor's first stage 20. Negative charge has accumulated in the insulator 24, either due to careless handling or due to external circumstances. Negative charges in the insulator 24 cause a Coulombic attraction force to the positively charged particles in the flow 21, and pull the positively charged particles towards the insulator 24. FIG. 5 illustrates this attraction force with solid, unbroken arrows. The light the particle is, the easier it moves towards the insulator 24, due to the force effect. As the particle impinges the insulator, the particles clings to it and thus leaves the flow under observation.

FIG. 6 illustrates how positively charged particles, which cling to the insulator 24, produce around them a Coulombic force effect, which repels other positively charged particles. Due to this force effect small sized particles with a low mass do not follow the flow 21 through the holes in the nozzle parts 22, but separate from the flow and impinge either the lower surface of the cover part 26, nozzle part 22 or the walls of the stage 20. Should this be the second or higher stage of the impactor, in FIG. 6 the particles impinging the cover part 26 would naturally impinge the collector surface's lower surface in an earlier stage. Because the nozzle part 22 and the collector surface 23 are in electrical contact with the impactor's corresponding stage 20, a particle impinging the upper surface of the nozzle part 22, lower surface of the collector surface 23 or the stages 20 walls will cause a similarly detected current in the current measurement unit 15, as the same particle would if it impinged the collector surface 23 as the impactor's design originally intends.

Due to the losses that take place, part of the smaller particles collect to the stages, which are meant for larger particles, and transfer their charge to the stage in question. In this case the measured current is larger than the current caused by the charges of the larger particles alone. Hence, the number of particles which is estimated based on the measured current, differs from the real number of particles and causes a deviation in the measurement results.

Because the flow 21 transporting particles typically has to pass through several stages before it reaches the final stages, which collect the smallest particles, losses in the earlier stages can cause a significant difference in the fine particle content of the air flow 21 entering the impactor and in the fine particle content of the air flow 21 in the final stages of impactor. In this case the currents, which are measured in the final stages, and particle contents, which are estimated based on these measurements, can differ significantly from the real content of the flow 11 under observation.

SUMMARY OF THE INVENTION

The purpose of the invention is to achieve a new method and an apparatus for minimising Coulombic particle losses in impactors, and an impactor in which Coulombic particle losses have been minimised.

The advantage of the impactor and the method according to the invention compared to the prior art is an increase in the reliability of measurements caused by decrease in particle losses.

In addition, the method according to the invention will facilitate impactor assembly, as phases required to prevent charges in the insulators and to remove possibly produced charges can be completely left out or they can be simplified considerably.

In one embodiment of the method according to the invention Coulombic losses are minimised by placing an electrically conductive layer between the insulator and the flow transporting the particles. This type of electrically conductive layer can, at its simplest form, be realised with the help of a metal ring, which is placed on top of the insulator.

In another embodiment of the method according to the invention an electrically conductive layer can be realised by treating that surface of the insulator, which faces the flow with an electricity conductive substance. In this realisation there is no need for additional impactor parts.

In the third embodiment of the method according to the invention the force effect caused by the charges, which have accumulated in the insulator, towards the particles transported in the flow can be minimised, which is achieved by designing the insulator so, that the surface of the insulator is as far as possible from the flow transporting the particles.

In the fourth embodiment of the method according to the invention impactor's stage has been formed so, that a part of the stage is situated between the insulator and the flow, effectively forming an electrically conductive surface between the flow and the insulator of the conductive surface.

BRIEF DESCRIPTION OF THE DRAWINGS

The following describes the invention in detail by referring to the pictures enclosed out of which:

FIGS. 1, 2, 3, 4, 5 and 6 have been previously discussed in connection with the description of the prior art.

In the solution according to the method of the invention Coulombic losses in the impactor are minimised by restricting the force effect of the charges produced in the insulators 24 on the charged particles, which are transported in the flow 21.

Figure 1:
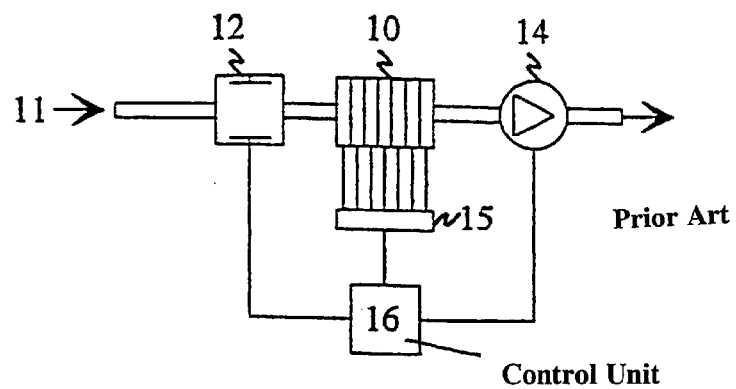
FIG. 1 presents a measuring system based on an electric impactor.
Figure 2:
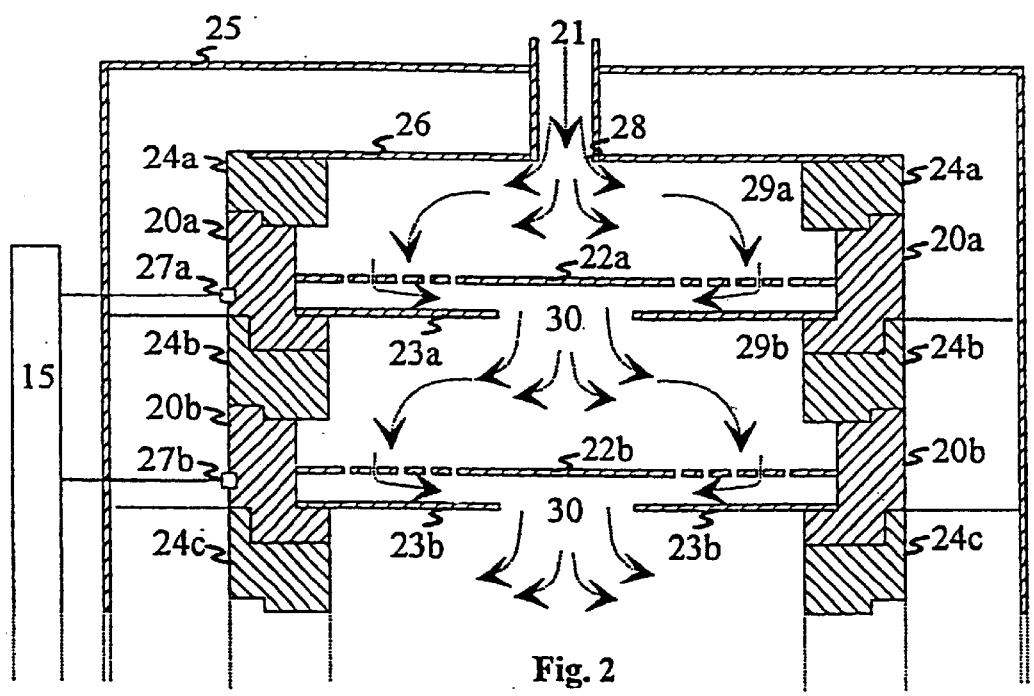
FIG. 2 presents the first two stages of an electric impactor.
Figure 3:
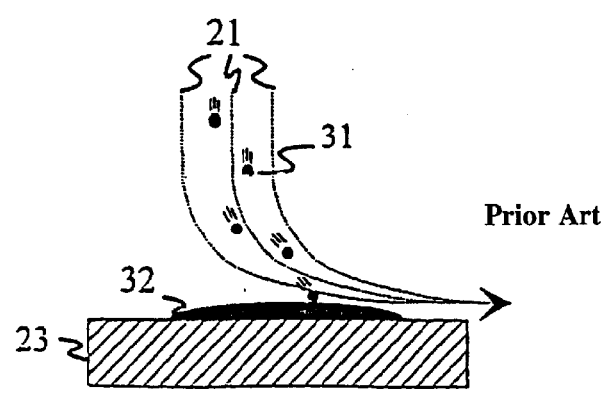
FIG. 3 presents how the particles impinge the collector surface.
Figure 4A:
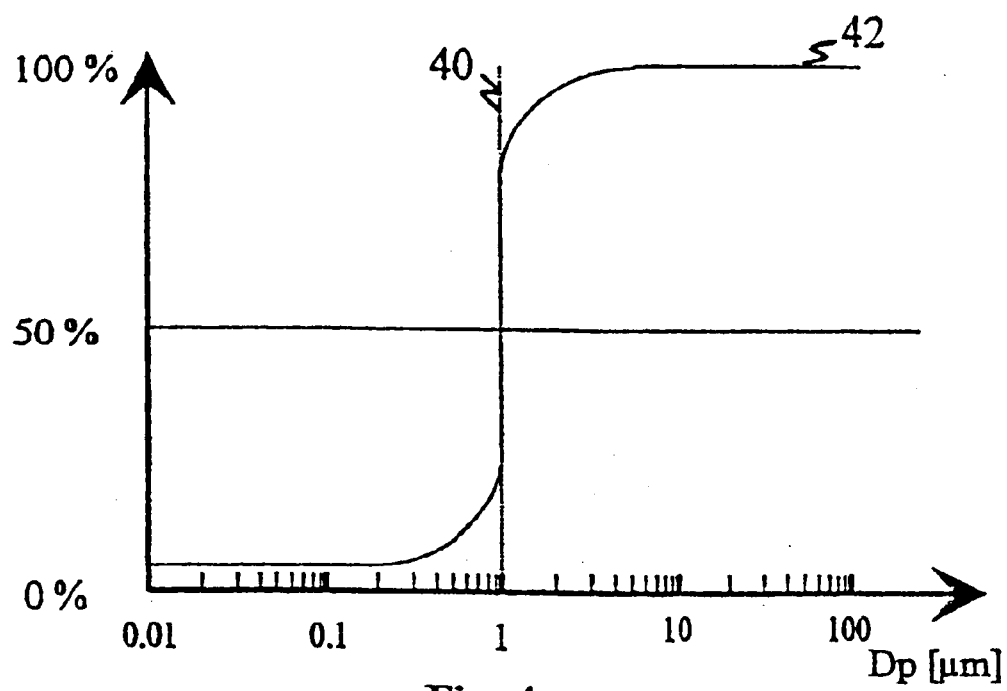
FIG. 4a and FIG. 4b presents the collection efficiency as function of particle size on one and more stages of the impactor.
Figure 4B:
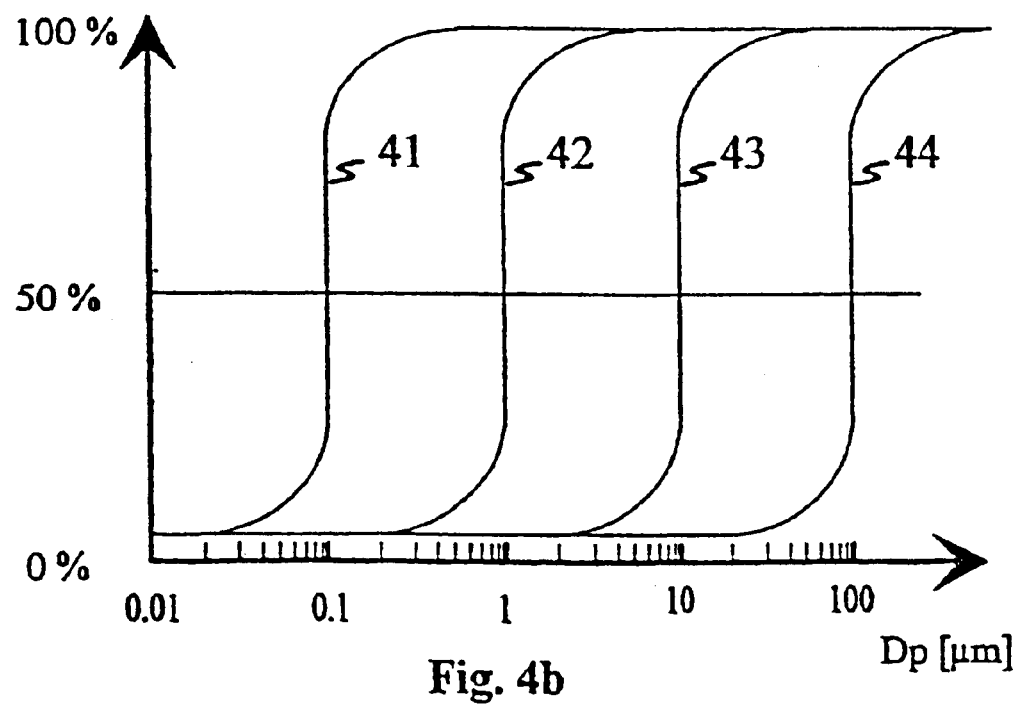
Figure 5:
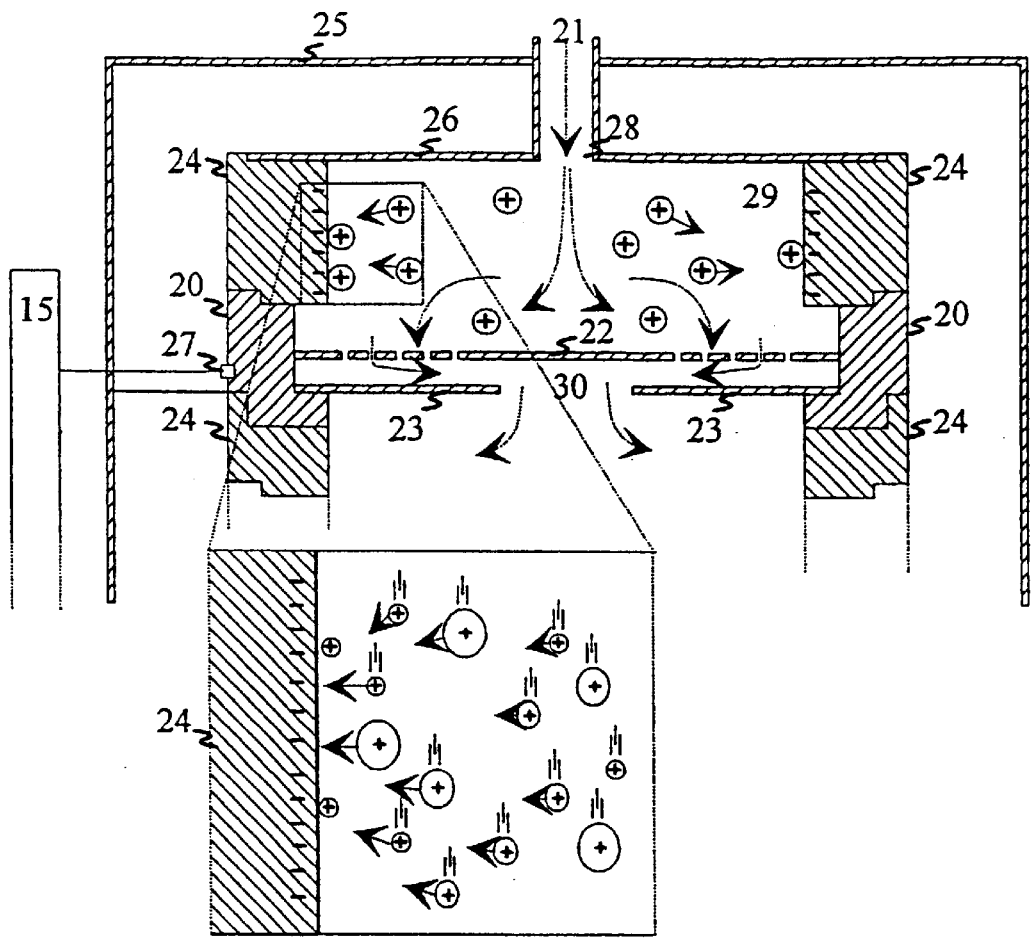
FIG. 5 presents the formation of a charge field, which causes Coulombic losses in the impactor.
Figure 6:
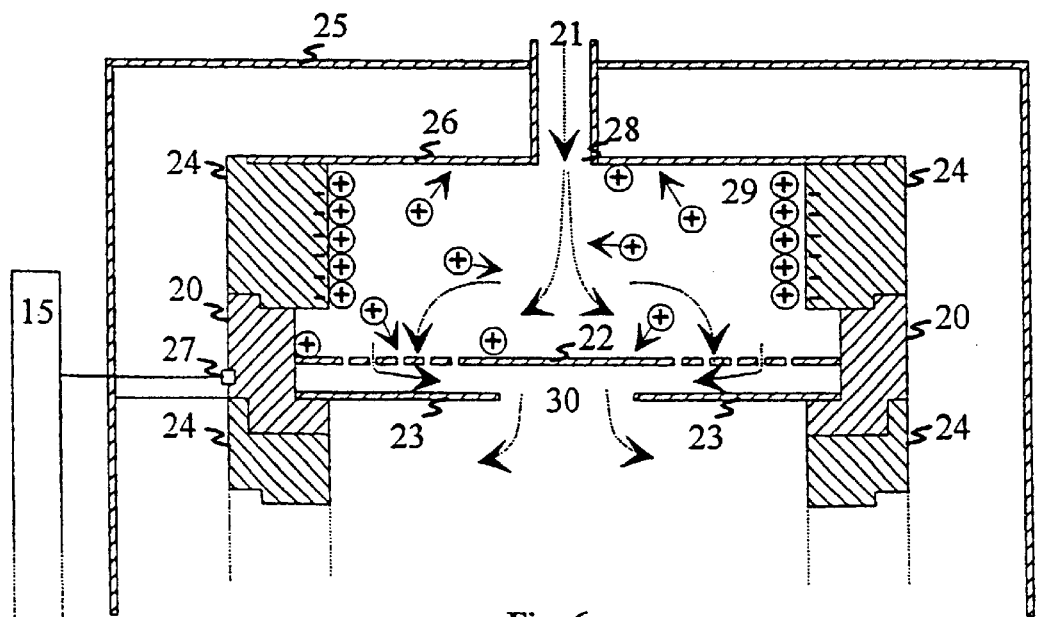
FIG. 6 presents the formation mechanism of Coulombic losses.
Figure 7:
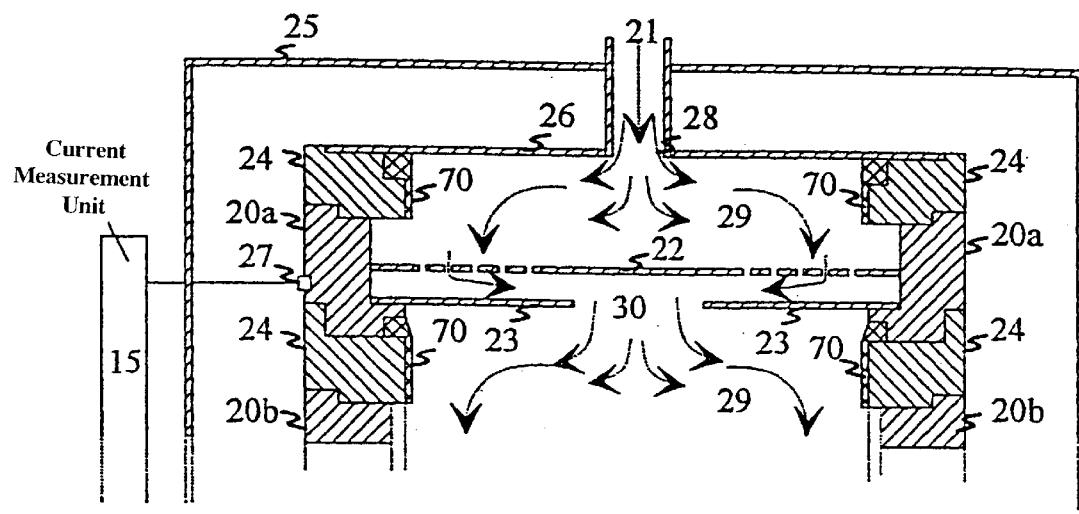
FIG. 7 presents one embodiment of the method according to the invention to minimise Coulombic particles losses.

FIG. 7 illustrates one solution to restrict said force effect. In this solution a ring 70 which, or at least its surface layer, conducts electricity, and which can be made of, for example, metal. The ring 70 is situated in the first chamber between the cover part 26 and the insulator 24 so, that the ring 70 is in electric contact with the cover part 26. In higher stages the ring 70 is situated between the stage 20a and the insulator 24 so, that the ring is in electric contact to the impactor's stage 20a, but not with the impactor's next stage 20b. In addition, the ring 70 is formed so that it produces an electrically conductive layer between the insulator 24 and the flow 21. Thus, the charged particles transported by the flow 21 do not "see" the charges in the insulator 24, because the electrically conductive layer of the ring 70 in front of the particles shadows the insulator's 24 charges and prevents the electrical field caused by them from reaching the flow 21. For this reason the charged particles do not experience the force effect towards the insulator 24; also, for which reason a positive charge cloud does not collect on the surfaces of the insulator, as presented in FIG. 6. Because the positive charge cloud is not formed, the particles transported in the flow 21 do not experience Coulombic repulsion force. Due to the lack of the repulsion force, even small charged particles remain in the flow 21 and there are no Coulombic losses produced.

An electrically conductive layer, which is situated between the insulator 24 and the flow 21, can also be realised by producing the impactor's stage 20*a* so, that the ring 70 would be an integral part of the impactor's stage 20*a*, as presented in FIG. 7, and not a separate ring. Furthermore, the solution according to the invention is not dependent on the fact whether the electrically conductive layer is connected to the stage preceding or succeeding the insulator.

Figure 8:
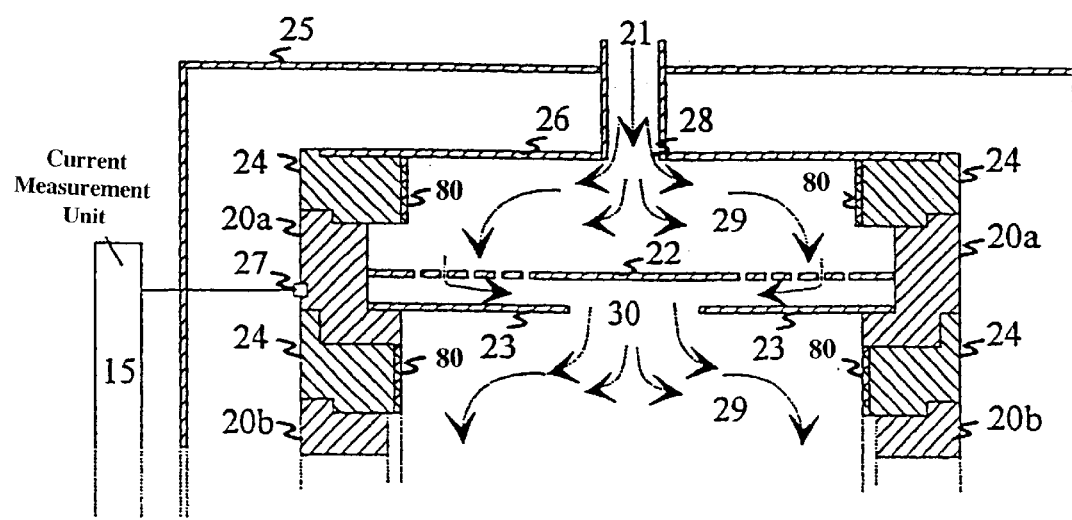
FIG. 8 presents another embodiment of the method according to the invention to minimise Coulombic particle losses.

FIG. 8 presents another embodiment of the solution according to the invention to minimise Coulombic losses. In this solution the insulator 24 is coated with electrically conductive material so, that the surface layer 80 is in electrical contact with the impactor's stage 20*a* or its cover part 26. Then the surface layer 80 acts correspondingly to a separate, electrically conductive layer as seen in FIG. 7, and prevents the insulator's 24 electrical field caused by the charges from reaching the flow 21.

Figure 9:
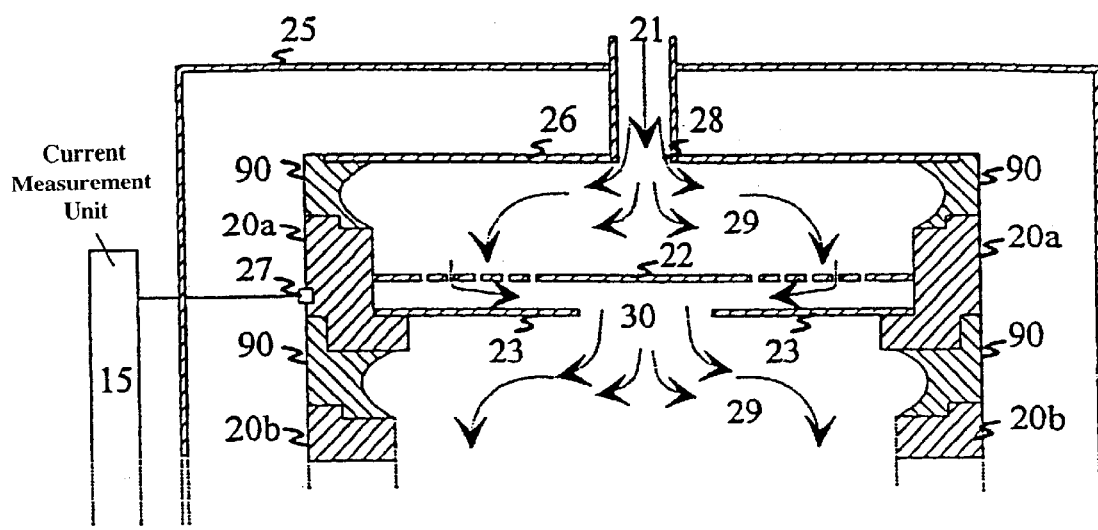
FIG. 9 presents a third embodiment of the method according to the invention to minimise Coulombic particle losses.

FIG. 9 presents a third embodiment of the method according to the invention to minimise Coulombic losses. In this solution impactor's insulator 90 has been formed so, that the surfaces which face the flow 21 are further away from the flow 21 than the surfaces of the impactor's stages 20*a* and 20*b*. Because Coulombic interaction weakens quadratically as distance grows, the force effect of negative charges formed in the insulator and, correspondingly, the force caused by the positively charged particles which collect on the surface of the insulator 90, is the smaller the further the surface of the insulator 90 is from the flow 21. By forming the insulator 90 so that its surface is as far away as possible from the flow 21 Coulombic losses can be minimised. The insulator 90 can be concave, as in FIG. 9, but man skilled in the art find it obvious that the form of the insulators can be realised in numerous ways within the scope of the invention so that the distance of the surface of the insulator 90 from the flow 21 is as long as possible.

The above-described detailed embodiments of the method and the impactor according to the invention are not, however, the only embodiments but can be varied within the scope of the claims. Especially, the form of the electrically conductive ring 70 and the insulator 90 can be realised in numerous different ways, within the scope of the claims. Furthermore, the embodiments of the method according to the invention or the impactor do not pose any restrictions on the design of the impactor's stages.

What is claimed is:

1. A method for measuring particle size distribution with an electrical impactor, comprising the steps of:

directing a flow transporting particles through an inlet to a chamber having side walls which comprise a stage, which is electrically connected to a current measurement unit, and an insulator which electrically insulates the stage from at least one of a frame section and from other stages;

directing in the chamber the flow through holes of a nozzle part which is essentially perpendicular to the flow and electrically connected to the stage;

deviating sharply the flow direction of the flow which has passed through the holes of the nozzle part by placing a collector surface, solid at the locations of the holes of the nozzle part, near the nozzle part after the nozzle part in the direction of the flow;

measuring an electrical current with the help of a current measurement unit which is electrically connected to the collector surface, said current being produced when out of the particles transported in the flow, particles which are larger than a desired size become detached from the flow as the flow direction changes sharply and impinge on the collector surface, thus transferring their charge to the collector surface; and direction the flow out of the chamber through at least one outlet, situated on the collector surface, wherein an electric field formed by charge accumulated on the insulator to the chamber on the route of the flow is minimized to minimize Coulombic losses of the charged particles.

2. Method according to claim 1, wherein the electric field is minimized by restricting said electrical field's access to the route of the flow.

3. Method according to claim 2, wherein the restriction is achieved through the design of the insulator.

4. Method according to claim 2, wherein the restriction is achieved by placing an electrically conductive layer between the insulator and the flow.

5. Electrical impactor for the measurement of particle size distribution, comprising:

at least one chamber having side walls which form a stage, which is electrically connected to a current measurement unit and an insulator to electrically insulate the stage from at least one of a frame part of the apparatus and other stages, an inlet to direct a flow to the chamber;

a nozzle part, which forms a base of the chamber and is essentially perpendicular to the stage and electrically connected to it, having holes through which the flow is directed;

a collector surface which is, in relation to the flow's direction, situated after the nozzle part and electrically connected to the stage, to which out of the particles transported in the flow, those particles which are larger than a desired size impinge as the direction of the flow changes sharply; and at least one outlet port to lead the flow at least one of on to a next chamber and out of the impactor, wherein at least one of the insulator itself and an electrically conductive layer situated between the insulator and the flow is designed so that the electrical field formed of the route of the flow by the charges accumulated on the insulator is minimized.

6. Impactor according to claim 5, wherein the layer which conducts electricity is a separate electrically conductive ring.

7. Impactor according to claim 6, wherein the electrically conductive ring is a metal ring.

8. Impactor according to claim 5, wherein the electrically conductive layer is a coating, which covers at least a part of the insulator and conducts electricity.

9. Impactor according to claim 5, wherein the insulator is designed so that its surface is further away from the flow transporting the charged particles than surfaces of the stage or the other stages.

10. Impactor according to claim 5, wherein the electrically conductive layer is an integral part of the stage.

* * * * *